United States Patent
Miyazawa

(10) Patent No.: US 10,052,222 B2
(45) Date of Patent: Aug. 21, 2018

(54) FINGER ASSISTIVE DEVICE

(71) Applicant: Seiko Epson Corporation, Tokyo (JP)

(72) Inventor: Osamu Miyazawa, Shimosuwa (JP)

(73) Assignee: Seiko Epson Corporation (JP)

( * ) Notice: Subject to any disclaimer, the term of this patent is extended or adjusted under 35 U.S.C. 154(b) by 259 days.

(21) Appl. No.: 14/493,491

(22) Filed: Sep. 23, 2014

(65) Prior Publication Data

US 2015/0094636 A1     Apr. 2, 2015

(30) Foreign Application Priority Data

Oct. 1, 2013   (JP) .................................. 2013-206153

(51) Int. Cl.
*A61F 5/01*         (2006.01)

(52) U.S. Cl.
CPC ...... *A61F 5/013* (2013.01); *A61F 2005/0155* (2013.01)

(58) Field of Classification Search
CPC .. A61F 5/05875; A61F 5/0118; A61F 13/105; A61F 5/10; A61F 5/05866; A61F 5/50; A61F 5/013; A61F 2005/0155; A61B 19/04; A41D 19/01588; A41D 13/087
USPC ..................................... 602/18; 128/879–880
See application file for complete search history.

(56) References Cited

U.S. PATENT DOCUMENTS

| | | | |
|---|---|---|---|
| 5,086,760 A | 2/1992 | Neumann et al. | |
| 5,376,091 A * | 12/1994 | Hotchkiss | A61B 17/62 602/22 |
| 7,105,984 B2 | 9/2006 | Miyazawa | |
| 8,585,625 B2 * | 11/2013 | Hegland | A61F 5/0118 602/22 |
| 8,668,659 B2 | 3/2014 | Kawakami | |
| 2009/0030356 A1 | 1/2009 | Maloney | |
| 2012/0150309 A1 | 6/2012 | Marissen | |
| 2012/0279342 A1 | 11/2012 | Yasukawa et al. | |
| 2013/0053738 A1 | 2/2013 | Kandt | |

FOREIGN PATENT DOCUMENTS

| | | |
|---|---|---|
| CN | 102858282 A | 1/2013 |
| JP | 07-163609 A | 6/1995 |
| JP | 11-192249 A | 7/1999 |
| JP | 2004-260990 A | 9/2004 |
| JP | 2008-520289 A | 6/2008 |

(Continued)

*Primary Examiner* — Ophelia A Hawthorne
(74) *Attorney, Agent, or Firm* — Harness, Dickey & Pierce, P.L.C.

(57) ABSTRACT

A finger assistive device is formed by connecting a second member to a first member so as to be rotatable in a bending direction of a finger. Further, either one of the first member and the second member is provided with a relative position changing section adapted to change a relative position of the second member to the first member in a direction different from the rotatable direction. According to this configuration, by changing the relative position of the second member to the first member in accordance with a length and a shape of the finger of the wearer, the finger assistive device can be customized (adjusted) so that the first member and the second member fit the mounting positions of the finger. As a result, it becomes possible to appropriately mount the finger assistive device to the finger and appropriately assist in bending the finger.

15 Claims, 13 Drawing Sheets

(56) References Cited

FOREIGN PATENT DOCUMENTS

| | | |
|---|---|---|
| JP | 2009-201648 A | 9/2009 |
| JP | 2010-063723 A | 3/2010 |
| JP | 2011-115248 A | 6/2011 |
| JP | 2012-082907 A | 4/2012 |
| JP | 2012-525551 A | 10/2012 |
| JP | 2012-235622 A | 11/2012 |

\* cited by examiner

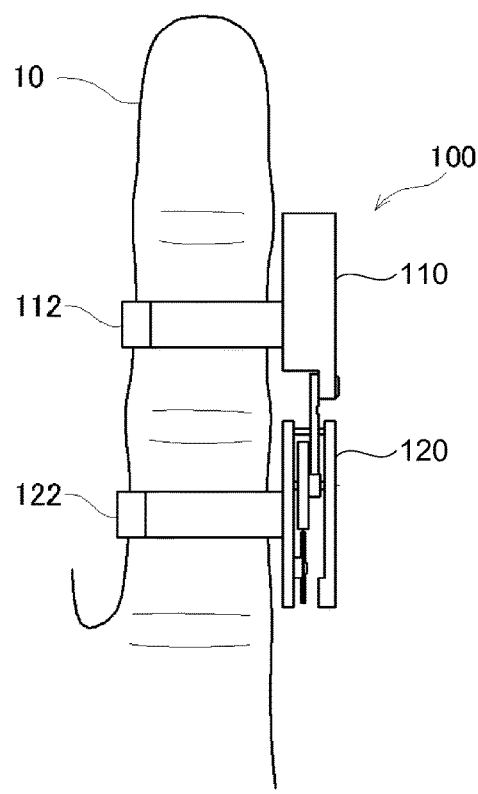
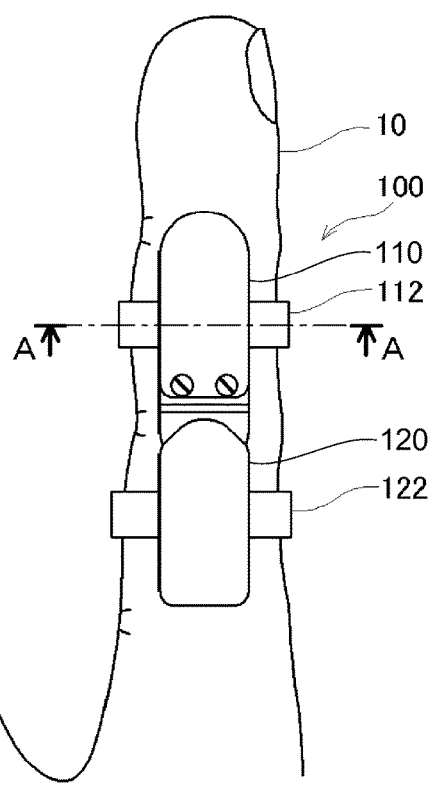
FIG. 1A  FIG. 1B
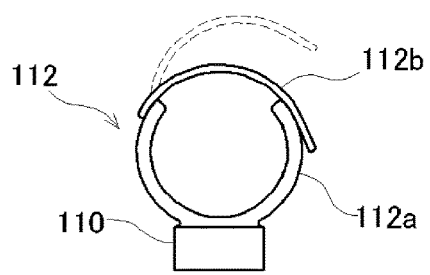
FIG. 1C

FINGER ASSISTIVE DEVICE

BACKGROUND

1. Technical Field

The present invention relates to a finger assistive device.

2. Related Art

There has been developed a device (a finger assistive device) attached to a finger by a person who has a trouble in bending and stretching a finger due to an accident or a disease, a person weakened in hand grip, or an older person who decreases in strength due to old age to thereby assist an action of the finger. For example, in JP-A-2011-115248, there is proposed a finger assistive device for assisting a flexing action of a finger by rotating a member attached along the finger in the bending direction of the finger.

However, in the finger assistive device proposed as described above, there is a problem that it is difficult to customize the finger assistive device in accordance with an individual variation such as variations in the length and shape of the finger of the wearer. Further, if the finger assistive device standardized with specific dimensions and shapes is used without modification, appropriate mounting is not achievable, and there is a possibility that it is difficult to bend and stretch the finger, or a load is applied to the finger.

SUMMARY

An advantage of some aspects of the invention is to provide a finger assistive device, which can be customized in accordance with the length or the shape of a finger of the wearer.

A finger assistive device according to an aspect of the invention adopts the following configuration. That is, a finger assistive device to be mounted to a finger and adapted to assist a bending action of the finger includes a first member to be mounted to the finger, and a second member to be mounted to the finger, and connected to the first member so as to be rotatable in a bending direction of the finger, and either one of the first member and the second member includes a relative position changing section adapted to change a relative position of the second member to the first member in a direction different from the rotatable direction.

In such a finger assistive device according to this aspect of the invention, it is possible to change the relative position of the second member to the first member independently of the action of the second member rotating in the bending direction of the finger. Therefore, by changing the relative position of the second member to the first member in accordance with a length and a shape of the finger of the wearer, the finger assistive device can be customized (adjusted) so that the first member and the second member fit the mounting positions of the finger. As a result, it becomes possible to appropriately mount the finger assistive device to the finger and appropriately assist in bending the finger.

In the finger assistive device according to the aspect of the invention described above, the relative position changing section may be provided to the second member, and the first member and the relative position changing section may be rotatably connected to each other.

Since such a relative position changing section is disposed along a part (a joint) where the finger bends, in the case in which the joint of the finger of the wearer is deformed (e.g., the joint is bent in a direction different from the bending direction), it become possible to customize the finger assistive device so as to fit the shape of the joint.

In the finger assistive device according to the aspect of the invention described above, the relative position changing section may make bending deformation to thereby change the relative position of the second member to the first member.

According to this configuration, even in the case in which the finger of the wearer is tilted in a direction different from the bending direction, by bending the relative position changing section in accordance with the tilt of the finger, it becomes possible to customize the finger assistive device so that the first member and the second member fit the mounting positions of the finger.

In the finger assistive device according to the aspect of the invention described above, the relative position changing section may make torsional deformation to thereby change the relative position of the second member to the first member.

According to this configuration, even in the case in which the finger of the wearer is twisted, by twisting the relative position changing section in accordance with the torsion of the finger, it becomes possible to customize the finger assistive device so that the first member and the second member fit the mounting positions of the finger.

In the finger assistive device according to the aspect of the invention described above, the relative position changing section may make plastic deformation to thereby change the relative position of the second member to the first member.

According to this configuration, once the finger assistive device is customized so as to fit the shape of the finger of the wearer, the shape is kept. Therefore, in the case of subsequently mounting the finger assistive device to the finger, no adjustment is necessary, and thus, quick mounting can be realized.

In the finger assistive device according to the aspect of the invention described above, the relative position changing section may be provided with a groove.

According to this configuration, since in the portion provided with the groove, the rigidity is lower than in other portions, and the stress is concentrated, it becomes possible to make the deformation in the relative position changing section easy, and at the same time, suppress the deformation in other portions than the relative position changing section.

In the finger assistive device according to the aspect of the invention described above, the relative position changing section may be provided with a cutout.

According to this configuration, since in the portion adjacent to the cutout, the rigidity is lower than in other portions, and the stress is concentrated, it becomes possible to make the deformation in the relative position changing section easy, and at the same time, suppress the deformation in other portions than the relative position changing section.

In the finger assistive device according to the aspect of the invention described above, the relative position changing section may be provided with a through hole.

According to this configuration, since in the portion adjacent to the through hole, the rigidity is lower than in other portions, and the stress is concentrated, it becomes possible to make the deformation in the relative position changing section easy, and at the same time, suppress the deformation in other portions than the relative position changing section.

In the finger assistive device according to the aspect of the invention described above, the through holes in the relative position changing section may be arranged in a predetermined direction.

According to this configuration, since it becomes easy to cause the deformation along the predetermined direction, it becomes possible to previously provide a direction to the deformation in the relative position changing section.

In the finger assistive device according to the aspect of the invention having the through hole in the relative position changing section described above, the through hole may be formed to have an elongated shape elongated in the predetermined direction.

According to this configuration, since it becomes easy to cause the deformation along the predetermined direction, it becomes possible to previously provide a direction to the deformation in the relative position changing section.

In the finger assistive device according to the aspect of the invention described above, the relative position changing section may be formed of a material low in rigidity compared to a part other than the relative position changing section in one of the first member and the second member.

According to this configuration, since the stress is concentrated in the relative position changing section low in rigidity in one of the first member and the second member, it becomes possible to make the deformation in the relative position changing section easy, and at the same time, suppress the deformation in other portions than the relative position changing section.

In the finger assistive device according to the aspect of the invention described above, the relative position changing section may expand and contract a distance between the first member and the second member.

According to this configuration, by expanding and contracting the distance between the first member and the second member in accordance with the length of the finger of the wearer, it becomes possible to customize the finger assistive device so that the first member and the second member fit the mounting positions of the finger.

The finger assistive device according to the aspect of the invention described above may be configured as follows. Firstly, a third member to be mounted to one of the finger and a base of the finger, and connected to the second member so as to be rotatable in the bending direction of the finger is provided. Further, either one of the second member and the third member is provided with a relative position changing section adapted to change a relative position of the third member to the second member in a direction different from the rotatable direction.

According to this configuration, in the finger assistive device for assisting in bending the two joints of the finger, by changing the relative position of the second member to the first member and the relative position of the third member to the second member in accordance with the length and the shape of the finger, the finger assistive device can be customized so that the first through third members fit the mounting positions of the finger or the base of the finger. As a result, it becomes possible to appropriately assist in bending the two joints of the finger.

The finger assistive device according to the aspect of the invention may be configured as follows. Firstly, a fourth member to be mounted to the base of the finger, and connected to the third member to be mounted to the finger so as to be rotatable in the bending direction of the finger is provided. Further, either one of the third member and the fourth member is provided with a relative position changing section adapted to change a relative position of the fourth member to the third member in a direction different from the rotatable direction.

According to this configuration, in the finger assistive device for assisting in bending the three joints of the finger, by changing the relative position of the second member to the first member, the relative position of the third member to the second member, and the relative position of the fourth member to the third member in accordance with the length and the shape of the finger, the finger assistive device can be customized so that the first through fourth members fit the mounting positions of the finger or the base of the finger. As a result, it becomes possible to appropriately assist in bending the three joints of the finger.

The aspect of the invention may also be configured out as the following aspects. That is, the invention may be configured as a finger assistive device including a first member, and a second member connected to the first member so as to be rotatable in a predetermined direction, wherein either one of the first member and the second member includes a relative position changing section adapted to change a relative position of the second member to the first member in a direction different from the rotatable direction, the first member includes a first ring-like section in which a finger can be inserted, and the second member includes a second ring-like section in which a finger can be inserted.

In such a finger assistive device according to this aspect of the invention, since the relative position of the second member to the first member can be changed separately from the predetermined rotatable direction, it becomes possible to customize (adjust) the finger assistive device so as to fit the shape of the finger inserted in the first ring-like section and the second ring-like section.

Here, focusing attention on the third joint of the finger, it is possible not only to be used in a simple bending action in the gripping direction but also to be moved in a number of directions including a direction (opening and closing direction) of opening and closing the fingers. Therefore, when attempting to assist the third joint of the finger, the finger assistive device having the only one movable direction, namely the bending direction of the finger, cannot cope with the motion of the third joint, and there is a problem that the motion of the third joint is limited by wearing the finger assistive device.

In order to make it possible to cope with such a motion of the third joint of the finger, the finger assistive device according to the aspect of the invention may also be configured as the following aspect. That is, a finger assistive device as another aspect of the invention is a finger assistive device adapted to assist a bending action of a finger including a first member to be mounted to the finger, and a second member to be mounted between a base of the finger and a wrist, and connected to the first member so as to be rotatable in a bending direction of the finger, wherein either one of the first member and the second member includes a relative position changing section adapted to change a relative position of the second member to the first member in a direction different from the rotatable direction.

In such a finger assistive device, when moving the third joint of the finger in a direction different from the bending direction in a state of mounting the finger assistive device, the relative position of the second member to the first member is changed by the relative position changing section in the direction different from the rotatable direction (the bending direction), and therefore, it is possible to make the finger assistive device follow the motion of the third joint of the finger. By increasing the movable directions of the finger assistive device in which the finger assistive device follows the motion of the third joint of the finger, it becomes possible to assist in bending the third joint without hindering the motion of the third joint toward the direction other than the bending direction of the finger.

In the finger assistive device described above, the relative position changing section may make plastic deformation to thereby change the relative position of the second member to the first member.

According to this configuration, if the relative position changing section deforms in accordance with the motion of the third joint to the direction other than the bending direction of the finger, when restoring the third joint, it becomes possible to make the finger assistive device follow the motion of the third joint using the restoring force of the relative position changing section thus deformed.

In the finger assistive device described above, the relative position of the second member to the first member may be changed by the relative position changing section rotating in a direction different from the direction in which the second member can rotate with respect to the first member.

In such a finger assistive device, by combining two rotational actions capable of changing the relative position of the second member to the first member in the respective directions different from each other, it becomes possible to make the finger assistive device follow the motion of the third joint of the finger in a number of directions.

BRIEF DESCRIPTION OF THE DRAWINGS

The invention will be described with reference to the accompanying drawings, wherein like numbers reference like elements.

FIGS. 1A through 1C are explanatory diagrams showing an appearance of a finger assistive device according to a first embodiment of the invention attached to an index finger of a human hand.

DESCRIPTION OF EXEMPLARY EMBODIMENTS

Figure 2A:
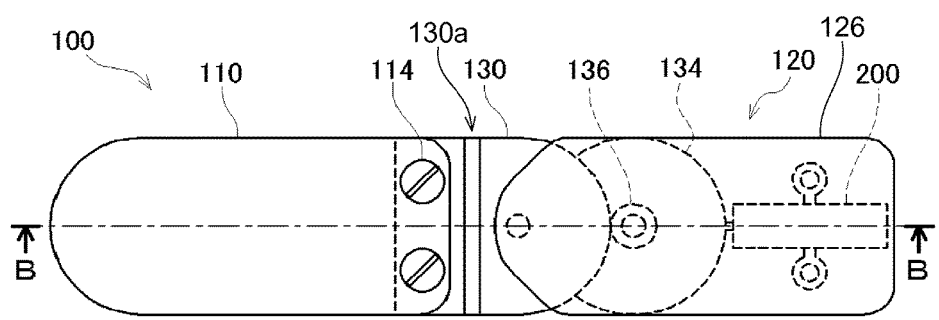
FIGS. 2A and 2B are explanatory diagrams showing a detailed structure of the finger assistive device according to the first embodiment.

FIGS. 1A through 1C are explanatory diagrams showing an appearance of a finger assistive device 100 according to a first embodiment of the invention attached to a finger (an index finger) 10 of a human hand. FIG. 1A shows a state viewed from a ball of the finger (a side of a surface forming an inner side when making a fist), and FIG. 1B shows a state viewed from a lateral side of the finger. It should be noted that the object wearing the finger assistive device 100 is not limited to the index finger of the human hand, but it is also possible for the finger assistive device 100 to be attached to other fingers of the hand, a toe, or a finger of a hand or a toe of a nonhuman animal.

As shown in the drawings, the finger assistive device 100 is provided with a first unit 110 and a second unit 120 connected in series to each other. The first unit 110 is provided with a first attachment section 112 to be attached to a side surface of a middle section (an intermediate between the first joint and the second joint) of the index finger 10, and the second unit 120 is provided with a second attachment section 122 to be attached to a side surface of a base section (an intermediate between the second joint and the third joint) of the index finger 10. Although a detailed structure of the finger assistive device 100 will be described later, it is arranged that the second unit 120 can rotate in the bending direction of the index finger 10 with respect to the first unit 110, and the finger assistive device 100 according to the first embodiment assists in bending and stretching the second joint of the index finger 10. It should be noted that the first unit 110 of the first embodiment corresponds to a "first member" according to the invention, and the second unit 120 of the first embodiment corresponds to a "second member" according to the invention.

The first attachment section 112 and the second attachment section 122 are arranged to be basically the same, and FIG. 1C shows a cross-sectional view in the case of cutting the first unit 110 at the position of the line A-A shown in FIG. 1B. As shown in FIG. 1C, the first attachment section 112 is provided with a circular arc section 112a formed to have a circular arc shape obtained by cutting a part far from the first unit 110, and a belt section 112b bridged from one end of the cutout portion of the circular arc section 112a to the other end thereof. The circular arc section 112a is formed of a hard material, while the belt section 112b is formed of a soft material such as rubber. It is arranged that one end of the belt section 112b is detachably attached to the circular arc section 112a using a surface fastener or the like, and by inserting the index finger 10 inside the circular arc section 112a in the state (the state indicated by the dotted line in the drawing) of detaching the belt section 112b, and then fixing the belt section 112b to the circular arc section 112a as indicated by the solid line in the drawing, the finger assistive device 100 can be attached to the index finger 10.

Figure 2B:
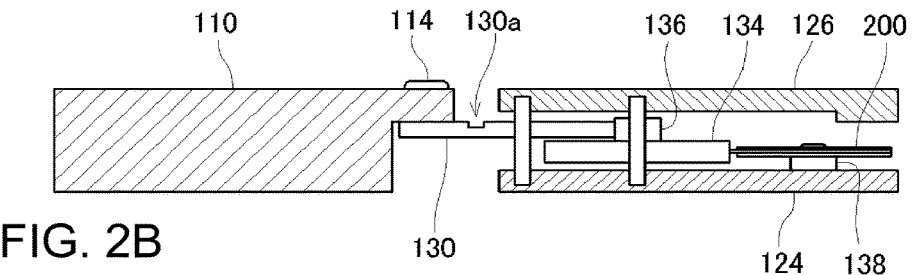

FIGS. 2A and 2B are explanatory diagrams showing a detailed structure of the finger assistive device 100 according to the first embodiment. It should be noted that in FIGS. 2A and 2B, the first attachment section 112 and the second attachment section 122 are omitted from the drawings. FIG. 2A is a front view of the finger assistive device 100 viewed from an opposite side to the side to be disposed along the index finger 10, and FIG. 2B is a cross-sectional view in the case of cutting the finger assistive device 100 at the position of the line B-B shown in FIG. 2A.

Firstly, the second unit 120 is provided with a lower frame plate 124 and an upper frame plate 126 arranged so as to be opposed to each other as shown in FIG. 2B, and the lower frame plate 124 is provided with the second attachment section 122 described above. An output member 130 as a metal flat plate formed to have a shape obtained by combining a rectangle and a semicircle with each other is disposed between the lower frame plate 124 and the upper frame plate 126 so as to be able to rotate around a center of the circular arc as an axis. To the rectangle side of the output member 130, the first unit 110 is connected with connection screws 114. Further, the output member 130 of the first embodiment is provided with a groove 130a, which is formed in a direction intersecting with a direction (a connection direction) in which the first unit 110 and the second unit 120 are connected in series to each other, disposed at a position between first unit 110 and the upper frame plate 126 of the second unit 120. It should be noted that the part of the first embodiment where the groove 130a is disposed corresponds to a "relative position changing section" according to the invention.

Further, between the lower frame plate 124 and the upper frame plate 126, there are disposed a rotor 134 having a disk-like shape rotating around an axis different from the axis of the output member 130, a spur gear 136 coaxially rotating together with the rotor 134, a piezoelectric motor 200 for rotating the rotor 134, and so on. On the outer circumference of the semicircle portion of the output member 130, there are disposed gear teeth (not shown) to be meshed with the spur gear 136, and when the rotor 134 rotates, the rotation propagates to the output member 130 via the spur gear 136 after being reduced at a predetermined ratio, and thus, the output member 130 is rotated.

The piezoelectric motor 200 is screwed on top surfaces of two bosses 138 each having a circular cylindrical shape and disposed so as to project from the lower frame plate 124, and has contact with the outer circumferential surface of the rotor 134. Further, to the piezoelectric motor 200, there is connected a drive control section (not shown) for controlling drive of the piezoelectric motor 200 by supplying a drive signal. Hereinafter, a structure of the piezoelectric motor 200 will be explained.

Figure 3:
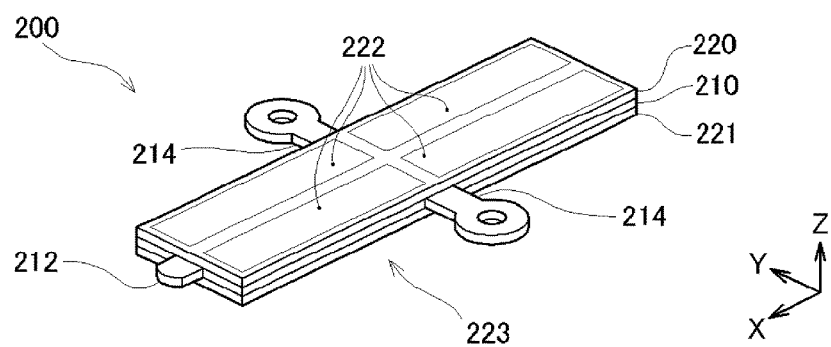
FIG. 3 is a perspective view showing a structure of a piezoelectric motor.

FIG. 3 is a perspective view showing the structure of the piezoelectric motor 200. As shown in the drawing, the piezoelectric motor 200 has a laminate structure obtained by sandwiching a shim plate 210 formed of a metal flat plate between two piezoelectric elements (an obverse piezoelectric element 220, a reverse piezoelectric element 221) each including a piezoelectric material and formed to have a plate shape, and then bonding the shim plate 210 and the piezoelectric elements to each other. Hereinafter, a longitudinal direction of the piezoelectric motor 200 is referred to as an X direction. Further, as shown in the drawing, it is assumed that a traverse direction of the piezoelectric motor 200 perpendicular to the X direction is referred to as a Y direction, and the thickness direction of the piezoelectric motor 200 perpendicular to both of the X direction and the Y direction is referred to as a Z direction.

On the surface (the upper surface) of the obverse piezoelectric element 220 opposite to the surface having contact with the shim plate 210, there are disposed obverse electrodes 222 for applying a voltage to the obverse piezoelectric element 220, and as shown in FIG. 3, there are four obverse electrodes 222 each having a rectangular shape so as to divide the upper surface of the obverse piezoelectric element 220 into four equal parts in a reticular pattern. Further, although not shown in the drawings, four reverse electrodes 223 each having a rectangular shape are similarly disposed on a surface (the lower surface) of the reverse piezoelectric element 221 opposite to the surface having contact with the shim plate 210 so as to divide the lower surface into four equal parts in a reticular pattern. Further, the shim plate 210 made of metal has not only a role of reinforcing the piezoelectric elements (the obverse piezoelectric element 220, the reverse piezoelectric element 221), but also a role as a common electrode for applying voltages to the obverse piezoelectric element 220 and the reverse piezoelectric element 221, and is connected to the ground.

In an end portion of the piezoelectric motor 200 in the longitudinal direction (the X direction), there is disposed a projection section 212. Further, on both of the side surfaces facing to the traverse direction (the Y direction) of the piezoelectric motor 200, there are disposed a pair of support sections 214 for supporting piezoelectric motor 200 in the state of being biased toward the side provided with the projection section 212. The projection section 212 and the support sections 214 are formed integrally with the shim plate 210.

Figure 4A:
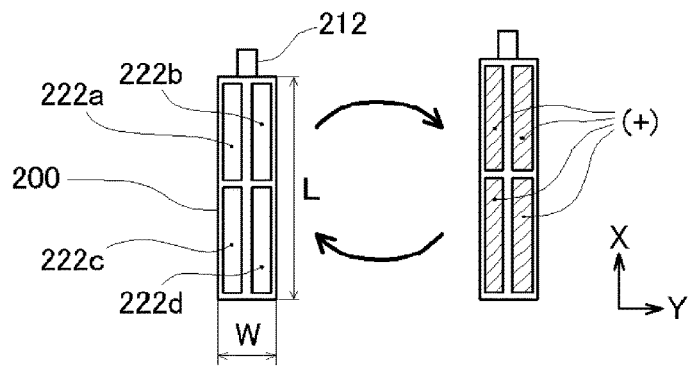
FIGS. 4A through 4C are explanatory diagrams showing a principle of operation of the piezoelectric motor.
Figure 4B:
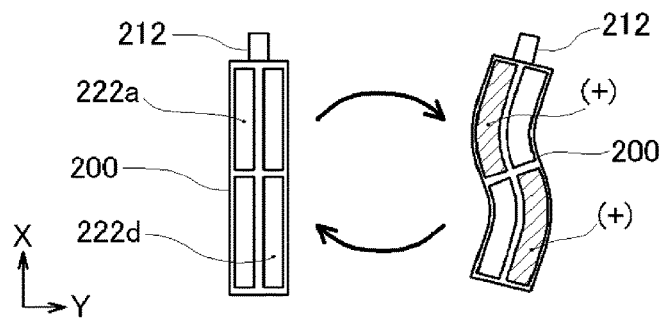
Figure 4C:
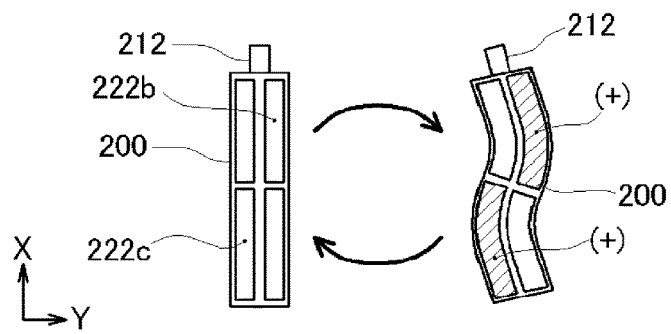

FIGS. 4A through 4C are explanatory diagrams showing a principle of operation of the piezoelectric motor 200. The piezoelectric motor 200 operates by the projection section 212 of the piezoelectric motor 200 making an elliptic motion when applying voltages to the obverse electrodes 222 and the reverse electrodes 223 with a regular period. The reason that the projection section 212 of the piezoelectric motor 200 makes the elliptic motion is as follows. It should be noted that since the obverse electrodes 222 disposed on the obverse piezoelectric element 220 and the reverse electrodes 223 disposed on the reverse piezoelectric element 221 are plane symmetric about the X-Y plane, and are basically the same, the obverse electrodes 222 will be explained here as an example.

Firstly, as well known to the public, the piezoelectric elements (the obverse piezoelectric element 220, the reverse piezoelectric element 221) including the piezoelectric material each have a property of contracting in response to application of a positive voltage. Therefore, as shown in FIG. 4A, by repeating an operation of applying a positive voltage to all of the four obverse electrodes 222 and then removing the applied voltage at a predetermined frequency, the piezoelectric motor 200 (the obverse piezoelectric element 220) can generate a kind of resonant phenomenon of expanding and contracting in the longitudinal direction (the X direction). It should be noted that the action of the piezoelectric motor 200 repeating the expansion and contraction in the longitudinal direction (the X direction) is referred to as a "longitudinal vibration," and the direction (±X direction in the drawing) in which the piezoelectric motor 200 expands and contracts is referred to as a "longitudinal direction."

Further, as shown in FIG. 4B or 4C, by applying a positive voltage at a specific frequency to a set (a set of the obverse electrodes 222a and 222d, or a set of the obverse electrodes 222b and 222c) of two obverse electrodes 222 located at diagonal positions, the piezoelectric motor 200 (the obverse piezoelectric element 220) can generate a kind of resonant phenomenon that a tip portion (a portion provided with the projection section 212) in the longitudinal direction (the X direction) yaws in a lateral direction (the Y direction) on the drawing. For example, as shown in FIG. 4B, when applying a positive voltage at a specific frequency to the set of the obverse electrodes 222a and 222d, the piezoelectric motor 200 repeats an action of the tip portion in the longitudinal direction moving rightward. Further, as shown in FIG. 4C, when applying a positive voltage at a specific frequency to the set of the obverse electrodes 222b and 222c, the piezoelectric motor 200 repeats an action of the tip portion in the longitudinal direction moving leftward. Such actions of the piezoelectric motor 200 are referred to as a "bending vibration," and the direction (±Y direction in the drawing) in which the piezoelectric motor 200 makes the bending vibration is hereinafter referred to as a "bending direction."

Further, by appropriately selecting the physicality of the obverse piezoelectric element 220 and the dimensions (the width W, the length L, and the thickness T) of the obverse piezoelectric element 220, it is possible to excite the resonance in the "longitudinal vibration" at the same time as making the piezoelectric motor 200 resonates in the "bending vibration." As a result, in the case of applying the voltage to the set of the obverse electrodes 222a and 222d in such a manner as shown in FIG. 4B, the tip portion (the portion provided with the projection section 212) of the piezoelectric motor 200 performs such an action (an elliptic motion) as to draw an ellipse clockwise on the drawing. Further, in the case of applying the voltage to the set of the obverse electrodes 222b and 222c in such a manner as shown in FIG. 4C, the tip portion of the piezoelectric motor 200 performs an elliptic motion in a counterclockwise direction. The same as in the case of the obverse piezoelectric element 220 is completely true for the reverse piezoelectric element 221.

The piezoelectric motor 200 drives a driven body using such an elliptic motion. Specifically, the piezoelectric motor 200 generates the elliptic motion in a state in which the projection section 212 of the piezoelectric motor 200 is pressed against the driven body. Then, the projection section 212 repeats an action of moving from left to right (or from right to left) in a state of being pressed against the driven body when the piezoelectric motor 200 expands, and returning to the initial position in a state of being separate from the driven body when the piezoelectric motor 200 contracts. As a result, the driven body is driven in one direction due to a frictional force applied by the projection section 212.

Figure 5:
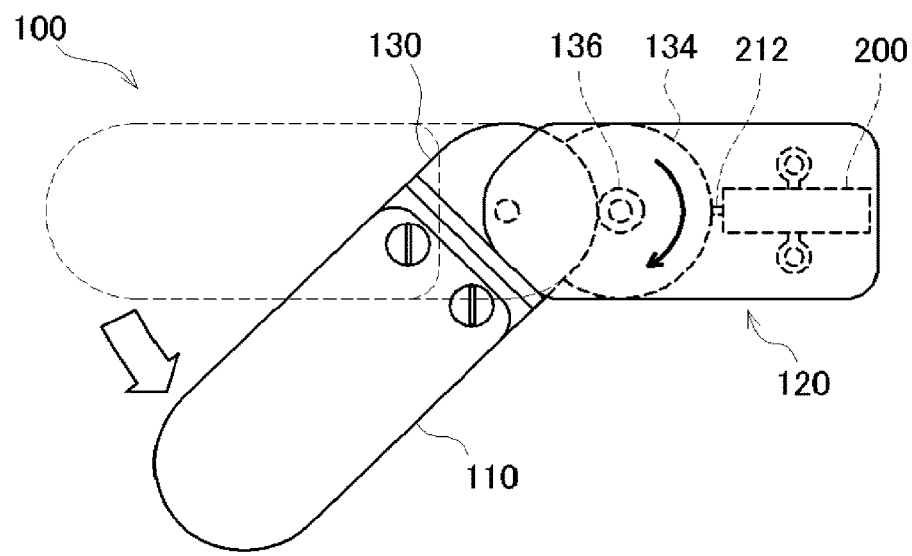
FIG. 5 is an explanatory diagram showing an operation of the finger assistive device.

FIG. 5 is an explanatory diagram showing an operation of the finger assistive device 100 due to the drive of the piezoelectric motor 200. The piezoelectric motor 200 mounted in the second unit 120 of the first embodiment is installed in a state in which the projection section 212 is pressed against the outer circumferential surface of the rotor 134. Therefore, when driving the piezoelectric motor 200, the rotor 134 is rotated, and the rotation propagates to the output member 130 via the spur gear 136. Further, since the first unit 110 is connected to the output member 130, it becomes possible to bend or stretch the first unit 110 with respect to the second unit 120 by driving the piezoelectric motor 200.

For example, as shown in FIG. 5, when driving the piezoelectric motor 200 so that the rotor 134 of the second unit 120 rotates clockwise on the drawing, the first unit 110 rotates counterclockwise to be flexed with respect to the second unit 120 as indicated by the outline arrow in the drawing. Further, if the piezoelectric motor 200 is driven in the opposite direction to rotate the rotor 134 counterclockwise on the drawing in the state in which the finger assistive device 100 is flexed, the first unit 110 rotates clockwise to be stretched with respect to the second unit 120.

In such a finger assistive device 100 according to the first embodiment, since the first unit 110 is attached to the side surface of the middle section of the index finger 10, the second unit 120 is attached to the base section of the index finger 10, and the second unit 120 rotates in the bending direction of the index finger 10 with respect to the first unit 110, it is possible to assist in bending and stretching the second joint of the index finger 10. It should be noted that it is also possible to assist in bending and stretching the second joint of the index finger 10 in a similar manner by arranging that the first unit 110 of the finger assistive device 100 is attached to the base section of the index finger 10 and the second unit 120 is attached to the middle section of the index finger 10. Further, it is also possible to assist in bending and stretching the first joint of the index finger 10 by attaching the first unit 110 and the second unit 120 of the finger assistive device 100 respectively to an end section (on the tip side of the first joint) and the middle section of the index finger 10.

Here, the shape of the finger varies between individuals, and is deformed, in some cases, due to injury or disease, for example, so that the part on the tip side from the second joint of the index finger 10 is tilted toward the middle finger. In such cases, the finger assistive device 100 standardized with a typical shape of index fingers may cause a problem that the finger assistive device cannot be attached, or a problem that it is difficult to bend and stretch the finger, or a load is applied to the finger if the finger assistive device is forcedly attached. Therefore, the finger assistive device 100 according to the first embodiment is arranged to be able to be deformed (customized) in accordance with the shape of the index finger 10 of the wearer.

Figure 6:
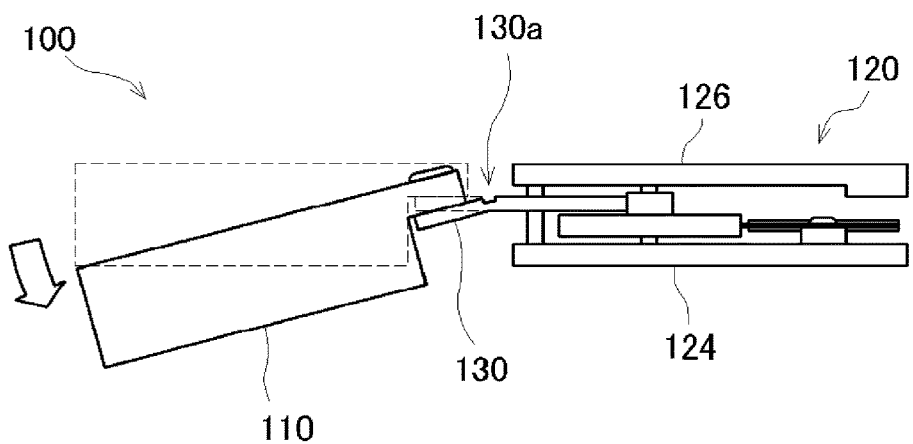
FIG. 6 is an explanatory diagram showing deformation of the finger assistive device for fitting the shape of the finger of the wearer.

FIG. 6 is an explanatory diagram showing the deformation of the finger assistive device 100 for fitting the shape of the finger of the wearer. As described above, in the finger assistive device 100 according to the first embodiment, the output member 130 formed of a metal flat plate is provided with the groove 130a formed in a direction intersecting with the connection direction, and the groove 130a is disposed at a position between the first unit 110 and the upper frame plate 126 of the second unit 120. If a predetermined force is applied to the first unit 110 in the direction (the direction intersecting with the direction in which the first unit 110 bends due to the rotation of the output member 130) of the outline arrow in the drawing in the state in which the second unit 120 is fixed, the stress is concentrated in a portion of the groove 130a low in rigidity in the output member 130, and therefore, the output member 130 plastically deforms along the groove 130a, and thus, it is possible to change the posture of the finger assistive device 100 to a bent posture.

As described above, in the finger assistive device 100 according to the first embodiment, it is arranged that the relative position of the first unit 110 to the second unit 120 can be changed (independently of the bending action of the finger assistive device 100) in a direction different from the bending direction of the finger assistive device 100 due to the rotation of the output member 130.

Figure 7:
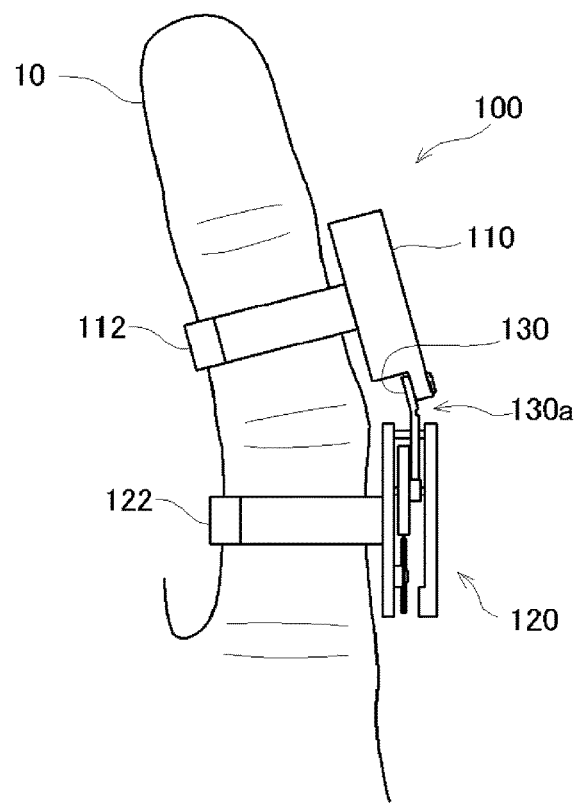
FIG. 7 is an explanatory diagram showing an appearance of the finger assistive device customized so as to fit a shape of the index finger and then attached to the index finger.

In such a finger assistive device 100 according to the first embodiment, even in the case in which the part on the tip side from the second joint of the index finger 10 is tilted toward the middle finger as in the example shown in FIG. 7, by bending the output member 130 at the position of the groove 130a, the finger assistive device 100 can be customized (adjusted) in accordance with the tilt of the second joint of the index finger 10 so that the first unit 110 fits the middle section of the index finger 10. As a result, it becomes possible to appropriately mount the finger assistive device 100 to the index finger 10 to assist in bending and stretching the second joint of the index finger 10.

Further, in the finger assistive device 100 according to the first embodiment, by providing the groove 130a to the output member 130, the rigidity of the portion of the groove 130a is lowered compared to the other portions, and therefore, it is possible to make the deformation (bending) in the predetermined position (the groove 130a) of the output member 130 easy, and at the same time, suppress deformation in other positions. It should be noted that since the direction in which the output member 130 deforms (bends) intersects with the direction in which the finger assistive device 100 is flexed due to the rotation of the output member 130, even if the output member 130 is bent so as to fit the shape of the index finger 10, the bending action of the finger assistive device 100 is not affected.

Further, since the output member 130 plastically deforms, once the finger assistive device 100 is customized so as to fit the shape of the index finger 10, the shape is kept. Therefore, in the case of subsequently mounting the finger assistive device 100 to the index finger 10, no adjustment is necessary, and thus, quick mounting can be realized.

There exist several modified examples of the finger assistive device 100 of the first embodiment described above. Hereinafter, these modified examples will simply be explained with a central focus on differences from the first embodiment. It should be noted that in the following modified examples, constituents in the intersection with the first embodiment will be attached with the same reference numerals, and thus, the detailed explanation thereof will be omitted.

Figure 8A:
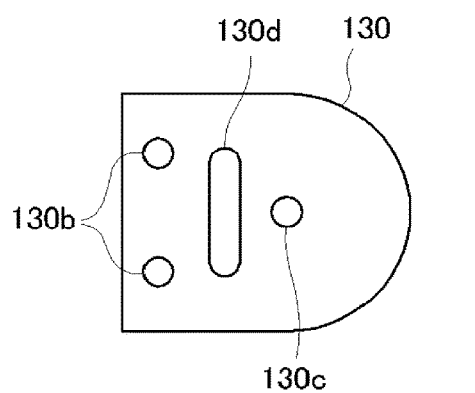
FIGS. 8A and 8B are explanatory diagrams each showing a shape of an output member provided to a finger assistive device according to a first modified example.
Figure 8B:
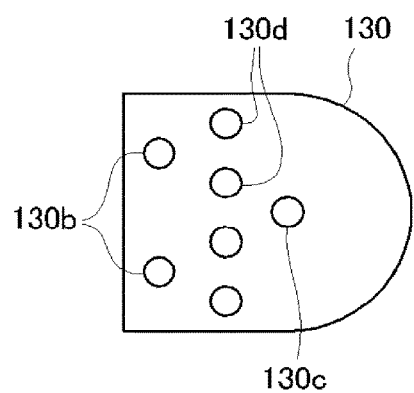

FIGS. 8A and 8B are explanatory diagrams each showing a shape of the output member 130 provided to the finger assistive device 100 according to a first modified example. Although the output member 130 of the first embodiment described above is provided with the groove 130a disposed at the position between connection screw holes 130b through which the connection screws 114 for connecting the output member 130 to the first unit 110 are inserted and a rotary shaft 130c, the output member 130 of the first modified example is provided with at least one through hole 130d instead of the groove 130a. FIG. 8A shows an example of disposing the through hole 130d having an elongated hole shape elongated in a direction intersecting with the connection direction, and FIG. 8B shows an example of disposing a plurality of through holes 130d arranged in a direction intersecting with the connection direction. It should be noted that the part of the first modified example where the through hole 130d is disposed corresponds to the "relative position changing section" according to the invention.

By providing the output member 130 with the through hole 130d in such a manner as described above, in the vicinity of the part where the through hole 130d is disposed, the rigidity is low compared to other parts, and the stress is concentrated, and therefore, it is possible to make it easy to deform (bend) the output member 130 at a predetermined position. Further, by arranging the through holes 130d in a predetermined direction, or providing the through hole 130d with the elongated hole shape, it becomes easy to cause the deformation along the predetermined direction, and therefore, it is possible to provide a direction to the deformation of the output member 130.

Figure 9A:
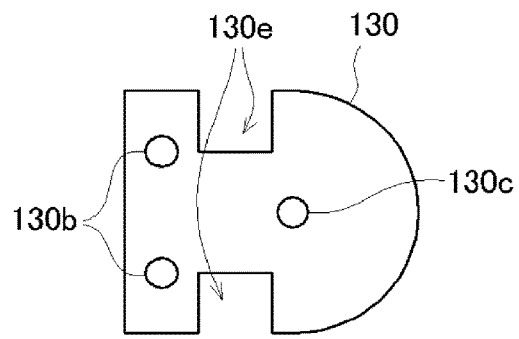
FIGS. 9A through 9C are explanatory diagrams showing a shape and deformation of an output member provided to a finger assistive device according to a second modified example.
Figure 9B:
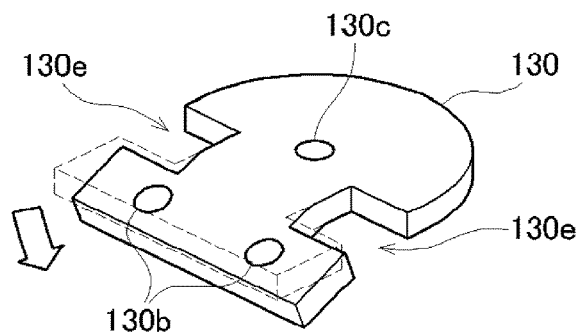
Figure 9C:
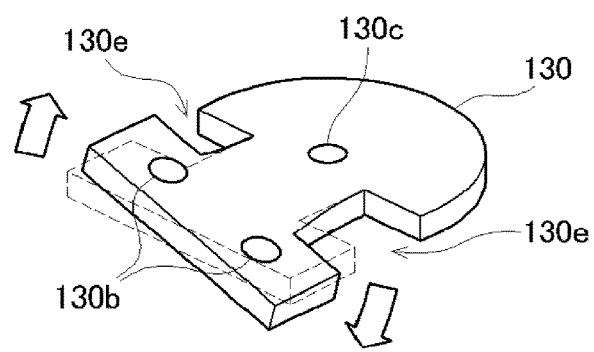

FIGS. 9A through 9C are explanatory diagrams showing a shape and deformation of the output member 130 provided to the finger assistive device 100 according to a second modified example. As shown in FIG. 9A, at a position between the connection screw holes 130b and the rotary shaft 130c of the output member 130 of the second modified example, there are disposed cutouts 130e on both sides in the direction intersecting with the connection direction, and the portion between the two cutouts 130e is narrower in width than other portions. It should be noted that the part of the second modified example where the cutouts 130e are disposed corresponds to the "relative position changing section" according to the invention.

By providing the output member 130 with the cutouts 130e in such a manner as described above, in the part between the two cutouts 130e, the rigidity in the direction (the direction intersecting with the direction in which the first unit 110 is bent due to the rotation of the output member 130) indicated by the outline arrow in FIG. 9B is lower than those in other parts, and the stress is easy to be concentrated, and therefore, the bending deformation of the output member 130 toward this direction becomes easy.

Further, as shown in FIG. 9C, in the part between the two cutouts 130e, the rigidity in the direction of twisting the rectangle side with respect to the semicircle side of the output member 130 is lower than other parts, and the stress is easily concentrated. Therefore, the torsional deformation of the output member 130 at the position where the cutouts 130e are disposed becomes easy. Therefore, even in the case in which the part on the tip side from the second joint of the index finger 10 of the wearer is twisted, by providing torsional deformation to the output member 130, it becomes possible to customize (adjust) the finger assistive device 100 so that the first unit 110 fits the side surface of the middle section of the index finger 10 in accordance with the torsion of the second joint of the index finger 10. It should be noted that regarding the groove 130a of the first embodiment described above and the through hole 130d of the first modified example, by setting the appropriate width in the connection direction, the torsional deformation of the output member 130 becomes easy.

Figure 10:
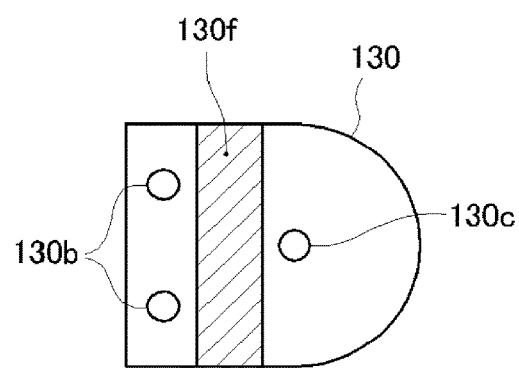
FIG. 10 is an explanatory diagram showing a structure of an output member provided to a finger assistive device according to a third modified example.

FIG. 10 is an explanatory diagram showing a structure of the output member 130 provided to the finger assistive device 100 according to a third modified example. The output member 130 of the third embodiment is not provided with the groove 130a, the through hole 130d, or the cutouts 130e, but is provided with a part (a low-rigidity part) 130f formed of a material lower in rigidity than other parts disposed between the connection screw holes 130b and the rotary shaft 130c instead of the groove 130a, the through hole 130d, or the cutouts 130e. It should be noted that the low-rigidity part 130f of the third modified example corresponds to the "relative position changing section" according to the invention. In the output member 130 provided with the low-rigidity part 130f as described above, since the stress is concentrated in the low-rigidity part 130*f*, it is possible to make the bending deformation or the torsional deformation of the output member 130 in the low-rigidity part 130*f* easy, and at the same time, suppress the deformation in other parts (the part where the connection screw holes 130*b*, the part where the rotary shaft 130*c* is disposed).

It should be noted that the deformation of the output member 130 for fitting the finger assistive device 100 with the shape of the index finger 10 is not limited to plastic deformation, but can also be elastic deformation. In the case of the elastic deformation, by attaching the first attachment section 112 and the second attachment section 122 of the finger assistive device 100 respectively to the middle section and the base section of the index finger 10 while deforming the output member 130 in accordance with the shape (the tilt and the torsion) of the index finger 10, the finger assistive device 100 can appropriately be mounted to the index finger 10. In contrast, in the case of the plastic deformation, the output member 130 can previously be deformed so as to fit the shape of the index finger 10.

Figure 11:
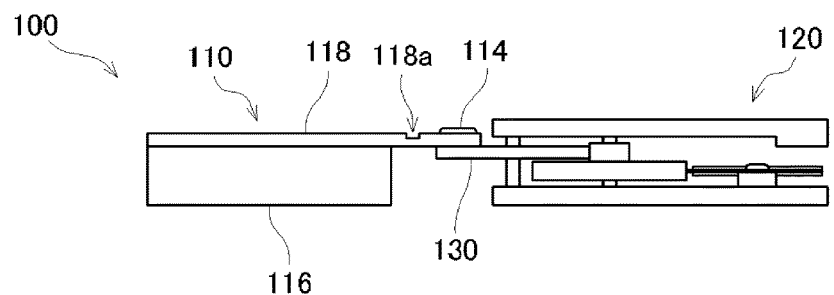
FIG. 11 is an explanatory diagram showing a structure of a finger assistive device according to a fourth modified example.

FIG. 11 is an explanatory diagram showing a structure of the finger assistive device 100 according to a fourth modified example. In the finger assistive device 100 according to the first embodiment described above, the output member 130 is provided with the groove 130*a*, while in the finger assistive device 100 according to the fourth modified example, a groove 118*a* is disposed on the first unit 110 side. As shown in FIG. 11, the first unit 110 of the fourth modified example is provided with a base body 116 on which the first attachment section 112 described above is disposed, and a connection plate 118 formed of a metal flat plate to be connected to the output member 130 with the connection screws 114. Further, the connection plate 118 is provided with the groove 118*a* formed in the direction intersecting with the connection direction disposed at a position between the base body 116 and the output member 130. The part of the fourth modified example where the groove 118*a* is disposed corresponds to the "relative position changing section" according to the invention.

In such a finger assistive device 100 according to the fourth modified example, since the rigidity of the portion of the groove 118*a* is low compared to other portions in the connection plate 118, the deformation (bending) of the connection plate 118 along the groove 118*a* in which the stress is concentrated becomes easy. Further, similarly to the first embodiment described above, in the finger assistive device 100 according to the fourth modified example, by providing the deformation to the connection plate 118, it is possible to customize (adjust) the finger assistive device 100 so that the base body 116 of the first unit 110 fits the side surface of the middle section of the index finger 10 in accordance with the shape of the second joint of the index finger 10.

It should be noted that although in the finger assistive device 100 according to the fourth modified example, there is shown an example of providing the connection plate 118 of the first unit 110 with the groove 118*a*, it is also possible to provide the connection plate 118 with the through hole, the cutouts, or the low-rigidity part as in the first through third modified examples described above to thereby make it easy to cause the bending deformation or the torsional deformation of the connection plate 118.

Figure 12A:
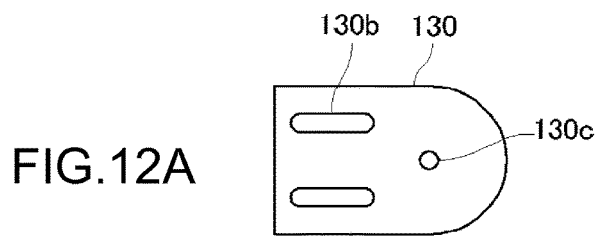
FIGS. 12A through 12C are explanatory diagrams showing a structure of a finger assistive device according to a fifth modified example.
Figure 12B:
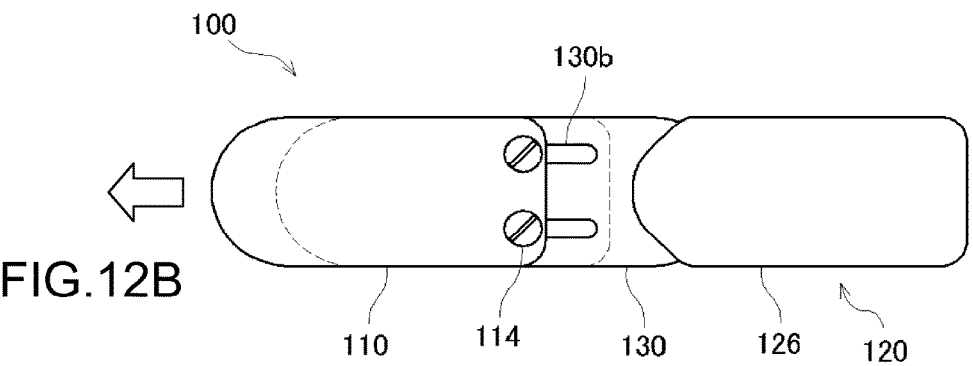
Figure 12C:
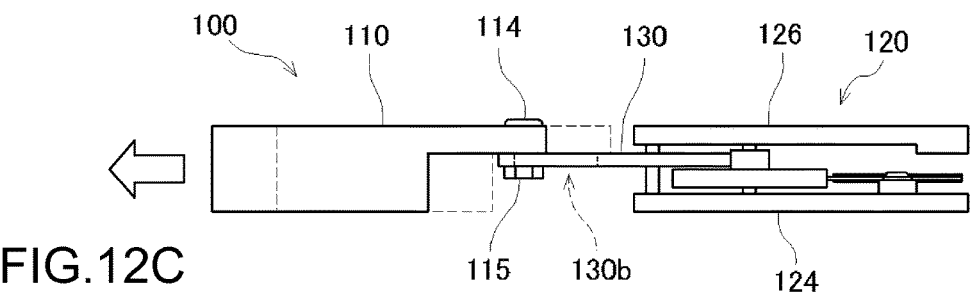

FIGS. 12A through 12C are explanatory diagrams showing a structure of the finger assistive device 100 according to a fifth modified example. Firstly, FIG. 12A shows a shape of the output member 130 provided to the finger assistive device 100 according to the fifth modified example. As shown in the drawing, in the output member 130 of the fifth modified example, the connection screw holes 130*b* are each formed to have an elongated hole shape elongated in the connection direction.

FIG. 12B shows a front view of the finger assistive device 100 viewed from an opposite side to the side to be fitted with the index finger 10, and FIG. 12C shows a side view of the finger assistive device 100. As shown in FIG. 12C, the first unit 110 and the output member 130 are connected to each other by being tightened with the connection screws 114 and connection nuts 115. Further, in the case in which the connection screws 114 are inserted on the side (left end in the drawing) far from the rotary shaft 130*c* in the connection screw holes 130*b* to connect the first unit 110 and the output member 130 to each other (in the state indicated by the solid line in the drawing), the distance between the first unit 110 and the upper frame plate 126 (the lower frame plate 124) can be made longer than in the case in which the connection screws 114 are inserted on the side (right end in the drawing) near to the rotary shaft 130*c* in the connection screw holes 130*b* (in the state indicated by the dotted line in the drawing). It should be noted that the connection screw holes 130*b* of the fifth modified example corresponds to the "relative position changing section" according to the invention.

In such a finger assistive device 100 according to the fifth modified example, by loosing the fastening with the connection screws 114 and the connection nuts 115, the positions of the connection screws 114 can be moved in the connection direction within the connection screw holes 130*b*. By changing (expanding and contracting) the distance between the first unit 110 and the upper frame plate 126 (the lower frame plate 124) in such a manner as described above, it is possible to customize (adjust) the finger assistive device 100 so that the first unit 110 is mounted at an appropriate position of the middle section of the index finger 10 in accordance with the length of the index finger 10 of the wearer.

Figure 13:
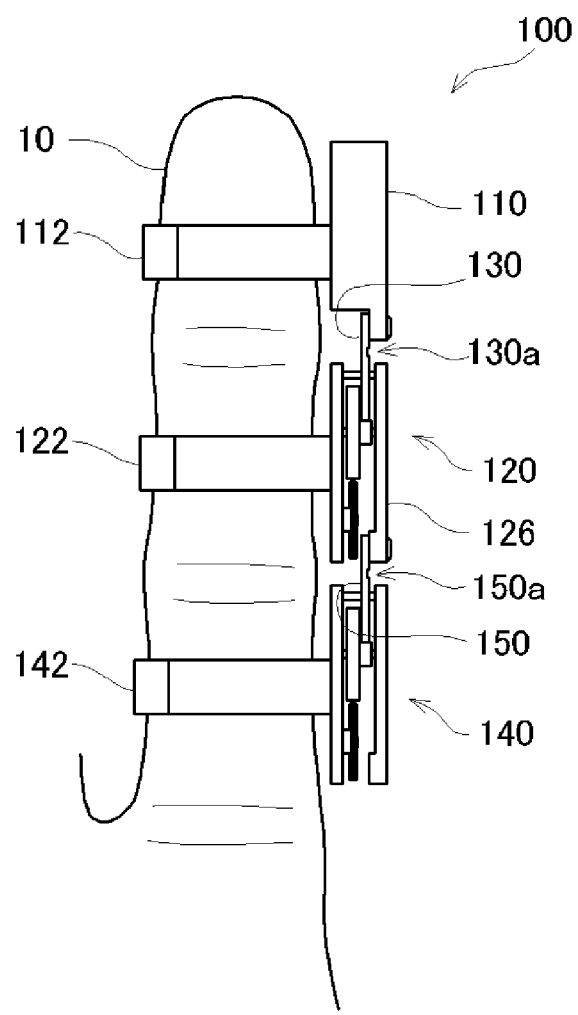
FIG. 13 is an explanatory diagram showing a structure of a finger assistive device according to a sixth modified example.

FIG. 13 is an explanatory diagram showing a structure of the finger assistive device 100 according to a sixth modified example. The drawing shows a state of the finger assistive device 100 according to the sixth modified example mounted on the index finger 10 viewed from a ball of the finger. As shown in the drawing, the finger assistive device 100 according to the sixth modified example is obtained by adding a third unit 140 to the finger assistive device 100 according to the first embodiment described above. The third unit 140 is arranged to be basically the same as the second unit 120, and the upper frame plate 126 of the second unit 120 and an output member 150 of the third unit 140 are connected to each other. It should be noted that the third unit 140 of the sixth modified example corresponds to the "third member" according to the invention. Further, a part of the output member 150 of the third unit 140 where a groove 150*a* is disposed corresponds to the "relative position changing section" according to the invention.

Further, the first unit 110 is attached to the end section of the index finger 10 with the first attachment section 112, the second unit 120 is attached to the middle section of the index finger 10 with the second attachment section 122, and the third unit 140 is attached to the base section of the index finger 10 with a third attachment section 142. Therefore, by driving the piezoelectric motor 200 mounted in the second unit 120, the second unit 120 rotates with respect to the first unit 110 to thereby make it possible to assist in bending and stretching the first joint. Further, by driving the piezoelectric motor 200 mounted in the third unit 140, the third unit 140 rotates with respect to the second unit 120 to thereby make it possible to assist in bending and stretching the second joint.

Also in such a finger assistive device 100 according to the sixth modified example, by deforming the output member 130 of the second unit 120 at the position of the groove 130a, and by deforming the output member 150 of the third unit 140 at the position of the groove 150a, the finger assistive device 100 can be customized (adjusted) so as to fit the shapes of the first joint and the second joint of the index finger 10 similarly to the finger assistive device 100 according to the first embodiment described above. As a result, it becomes possible to appropriately mount the finger assistive device 100 to the index finger 10 to assist in bending and stretching the first joint and the second joint of the index finger 10.

Although in the first embodiment and the modified examples of the first embodiment explained hereinabove, the finger assistive device 100 is mounted so as to assist in banding and stretching the second joint or the first joint of the index finger 10, it is also possible to attach the finger assistive device 100 so as to assist in bending and stretching a third joint (a base joint) of the index finger 10. Hereinafter, the finger assistive device 100 according to a second embodiment to be mounted so as to assist in bending and stretching the third joint of the index finger 10 will be explained. It should be noted that the second embodiment will be explained with a central focus on differences from the first embodiment, and the constituents in the intersection with the first embodiment will be attached with the same reference numerals, and thus, the detailed explanation thereof will be omitted.

Figures 14A, 14B:
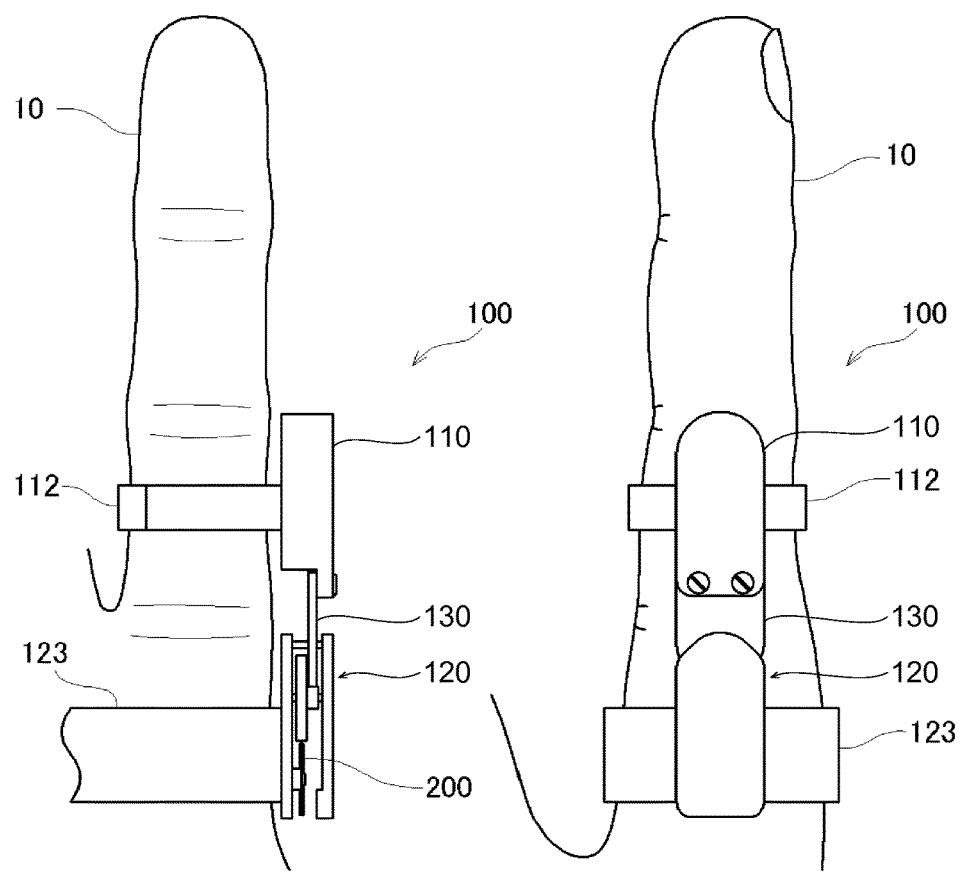
FIGS. 14A and 14B are explanatory diagrams showing an appearance of a finger assistive device according to a second embodiment of the invention mounted to the index finger.

FIGS. 14A and 14B are explanatory diagrams showing an appearance of a finger assistive device 100 according to the second embodiment mounted to the index finger 10. FIG. 14A shows a state viewed from a ball of the finger, and FIG. 14B shows a state viewed from a lateral side of the finger. The structure of the finger assistive device 100 according to the second embodiment is basically the same as that of the finger assistive device 100 according to the first embodiment described above, and has the first unit 110 and the output member 130 of the second unit 120 are connected to each other. It should be noted that the first unit 110 of the second embodiment is attached to the base section of the index finger 10 with the first attachment section 112, and the second unit 120 is attached between the third joint of the index finger 10 and the base of the thumb with an attachment belt 123 to be wound around the palm and the back of the hand.

In such a finger assistive device 100 according to the second embodiment, when driving the piezoelectric motor 200 mounted in the second unit 120, the second unit 120 rotates in the bending direction of the index finger 10 with respect to the first unit 110, and therefore, it is possible to assist in bending and stretching the third joint of the index finger 10. It should be noted that it is also possible to assist in bending and stretching the third joint of the index finger 10 in a similar manner by arranging that the first unit 110 of the finger assistive device 100 according to the second embodiment is attached between the third joint of the index finger 10 and the base of the thumb, and the second unit 120 is attached to the base section of the index finger 10.

Here, the third joint of the finger can not only be used in a simple bending action in the gripping direction but also be moved in a number of directions including a direction (opening and closing direction) of opening and closing the fingers. Therefore, the finger assistive device 100 having the only one movable direction, namely the bending direction of the index finger 10, cannot cope with the motion of the third joint, and the motion of the third joint of the index finger 10 is limited by wearing the finger assistive device 100. Therefore, in the finger assistive device 100 according to the second embodiment, it is arranged that the motion in other directions than the bending direction of the finger is possible in accordance with the motion of the third joint of the index finger 10.

Figure 15A:
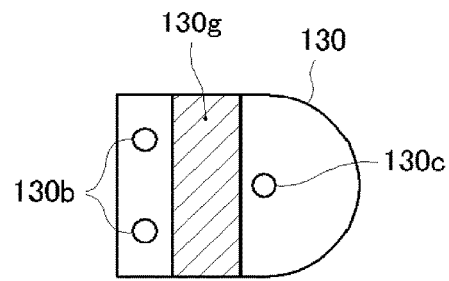
FIGS. 15A through 15C are explanatory diagrams showing a structure and deformation of an output member for acting in a direction other than the bending direction of the index finger in the finger assistive device according to the second embodiment.
Figure 15B:
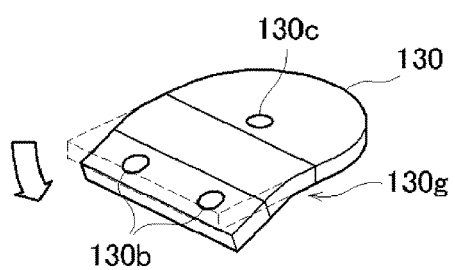
Figure 15C:
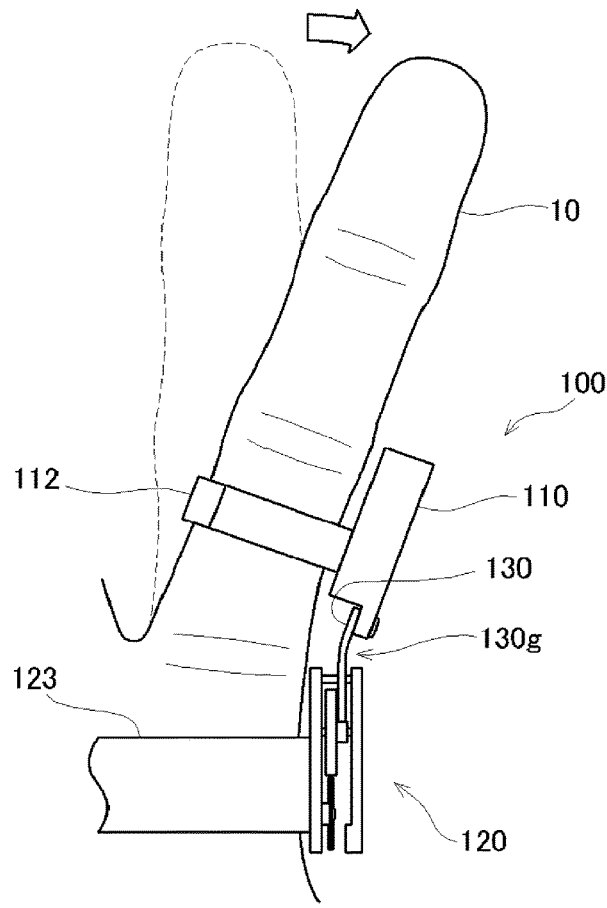

FIGS. 15A through 15C are explanatory diagrams showing a structure and deformation of the output member 130 for acting in a direction other than the bending direction of the index finger 10 in the finger assistive device 100 according to the second embodiment. As shown in FIG. 15A, the output member 130 of the second embodiment is provided with an elastically deformable section 130g disposed between the connection screw holes 130b and the rotary shaft 130c, and the elastically deformable section 130g is formed of a material lower in rigidity and easier to be elastically deformed than the material of other portions.

In the output member 130 provided with the elastically deformable section 130g in such a manner as described above, when a force is applied in the direction (a direction intersecting with the direction in which the first unit 110 bends due to the rotation of the output member 130) indicated by the outline arrow shown in FIG. 15B in a state in which the semicircle side is fixed, since the elastic deformation occurs in the elastically deformable section 130g in which the stress is concentrated, the output member 130 is bent in the direction of the force.

In such a finger assistive device 100 according to the second embodiment, when it is attempted to open the index finger 10 and the middle finger in the state of mounting the finger assistive device 100 in such a manner as shown in FIG. 15C, the output member 130 bends in a direction intersecting with the bending direction of the index finger 10. Thus, it is possible to change the relative position of the first unit 110 to the second unit 120 in the opening and closing direction (the direction of opening and closing the area between the index finger and the middle finger) of the index finger 10 to thereby make the finger assistive device 100 follow the motion of the third joint of the index finger 10 (it is possible to increase the movable directions for following the motion of the third joint of the index finger 10).

Further, in the finger assistive device 100 according to the second embodiment, by combining the action in the bending direction of the index finger 10 due to the rotation of the output member 130 and the action in the opening and closing direction of the index finger 10 due to the elastic deformation of the output member 130 with each other, it is possible to follow the motion of the third joint in the composite direction including the two directions, namely the bending direction of the index finger 10 and the opening and closing direction, and therefore, it becomes possible to assist in bending and stretching the third joint without hindering the motion of the third joint in directions other than the bending direction of the index finger 10.

Further, in the finger assistive device 100 according to the second embodiment, since the output member 130 is provided with the elastically deformable section 130g, if the elastically deformable section 130g elastically deforms in accordance with the motion of the third joint in the opening and closing direction of the index finger 10, when restoring the third joint, it becomes possible to make the finger assistive device 100 follow the motion of the third joint using the restoring force of the elastically deformable section 130*g* thus deformed.

It should be noted that although in the finger assistive device 100 according to the second embodiment, the output member 130 is provided with the elastically deformable section 130*g* to thereby make the elastic deformation easy, it is also possible to provide the output member 130 with a groove, a through hole, a cutout, or the like to thereby make the elastic deformation easy (see the first embodiment, the first modified example, and the second modified example described above). Further, it is also possible to make the elastic deformation of the first unit 110 easy by providing a groove, a through hole, a cutout, or an elastically deformable section to the first unit 110 instead of the output member 130 (see the fourth modified example of the first embodiment). Further, the configuration of the deformation of the output member 130 for making the finger assistive device 100 operable in directions other than the bending direction of the index finger 10 is not limited to the elastic deformation, but can also be a configuration of rotating in a direction different from the bending direction of the index finger 10.

Figure 16A:
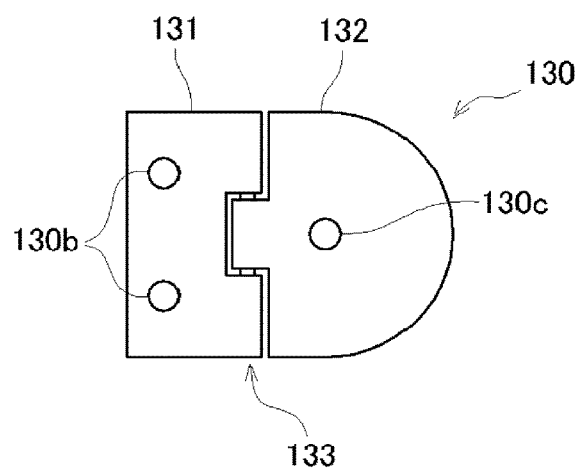
FIGS. 16A and 16B are explanatory diagrams showing an example of a structure of an output member capable of rotating in a direction different from the bending direction of the index finger.
Figure 16B:
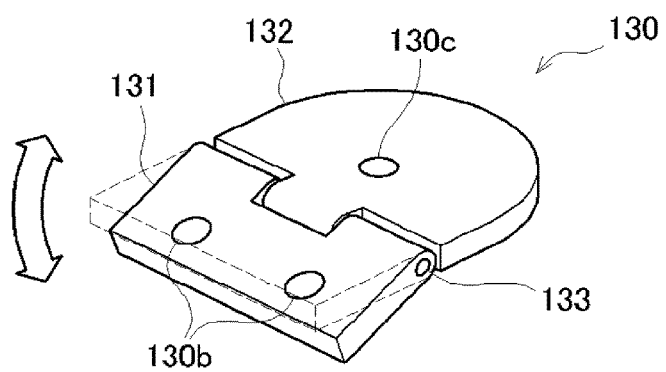

FIGS. 16A and 16B are explanatory diagrams showing an example of a structure of the output member 130 capable of rotating in a direction different from the bending direction of the index finger 10. As shown in FIG. 16A, the output member 130 thus shown as an example is provided with a rectangular section 131 provided with the connection screw holes 130*b*, and a semicircular section 132 provided with the rotary shaft 130*c*, and the rectangular section 131 and the semicircular section 132 are rotatably connected to each other with a connection shaft 133 intersecting with the connection direction and the axial direction of the rotary shaft 130*c*.

In the output member 130 having such a hinge structure, as indicated by the outline arrow in FIG. 16B, it is possible for the rectangular section 131 to rotate with respect to the semicircular section 132 in a direction intersecting with the rotational direction of the output member 130 around the rotary shaft 130*c*. Therefore, in the finger assistive device 100 provided with the output member 130 shown in FIGS. 16A and 16B, it becomes possible to act following the motion in the opening and closing direction of the third joint of the index finger 10. It should be noted that it is also possible to provide the hinge structure to the first unit 110 side instead of the output member 130 side.

Figure 17:
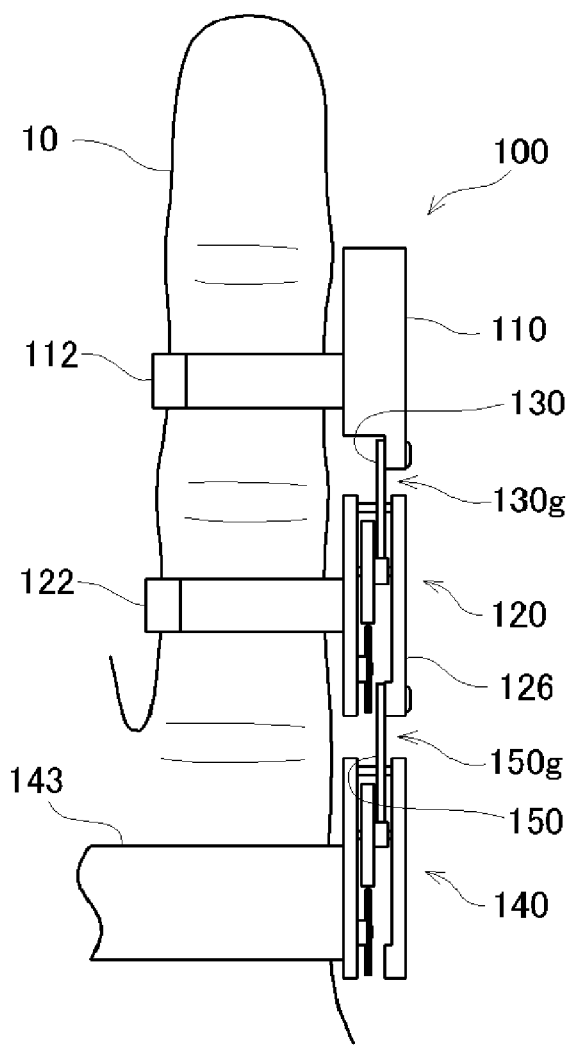
FIG. 17 is an explanatory diagram showing a finger assistive device for assisting in bending a second joint and a third joint of the index finger.

Further, in the finger assistive device 100 according to the second embodiment, it is also possible to arrange that bending and stretching of the second joint are also assisted in addition to bending and stretching of the third joint of the index finger 10. The finger assistive device 100 shown in FIG. 17 is obtained by adding the third unit 140 to the finger assistive device 100 shown in FIGS. 14A and 14B. The third unit 140 is arranged to be basically the same as the second unit 120, and the upper frame plate 126 of the second unit 120 and the output member 150 of the third unit 140 are connected to each other.

Further, the first unit 110 is attached to the middle section of the index finger 10 with the first attachment section 112, the second unit 120 is attached to the base section of the index finger 10 with the second attachment section 122, and the third unit 140 is attached between the third joint of the index finger 10 and the base of the thumb with an attachment belt 143. Therefore, by driving the piezoelectric motor 200 mounted in the second unit 120, the second unit 120 rotates with respect to the first unit 110 to thereby make it possible to assist in bending and stretching the second joint. Further, by driving the piezoelectric motor 200 mounted in the third unit 140, the third unit 140 rotates with respect to the second unit 120 to thereby make it possible to assist in bending and stretching the third joint.

The second joint of the finger can be moved in directions other than the bending direction to a lesser extent than the third joint. Therefore, since the finger assistive device 100 shown in FIG. 17 bends in a direction intersecting with the bending direction of the index finger 10 at the positions of the elastically deformable section 130*g* of the output member 130 of the second unit 120 and the elastically deformable section 150*g* of the output member 150 of the third unit 140, it becomes possible to assist in bending and stretching the second joint and the third joint without hindering the motion in directions other than the bending direction of the index finger 10. Further, by deforming the output member 130 of the second unit 120 at the position of the elastically deformable section 130*g* (or the hinge structure described above), the finger assistive device 100 can be customized (adjusted) so as to fit the shape of the second joint of the index finger 10 similarly to the first embodiment described above.

Figure 18:
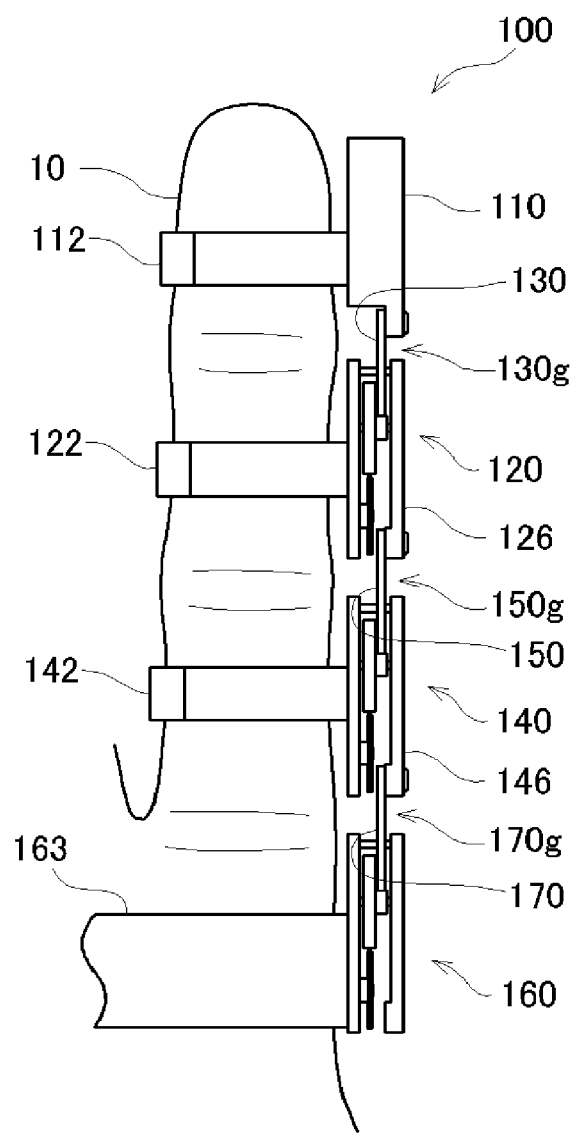
FIG. 18 is an explanatory diagram showing a finger assistive device for assisting in bending a first joint through a third joint of the index finger.

Further, the finger assistive device 100 shown in FIG. 18 is obtained by adding a fourth unit 160 to the finger assistive device 100 shown in FIG. 17. The fourth unit 160 is arranged to be basically the same as the second unit 120 and the third unit 140, and an upper frame plate 146 of the third unit 140 and an output member 170 of the fourth unit 160 are connected to each other. It should be noted that the fourth unit 160 corresponds to a "fourth member" according to the invention.

Further, the first unit 110 is attached to the end section of the index finger 10 with the first attachment section 112, the second unit 120 is attached to the middle section of the index finger 10 with the second attachment section 122, the third unit 140 is attached to the base section of the index finger 10 with the third attachment section 142, and the fourth unit 160 is attached between the third joint of the index finger 10 and the base of the thumb with an attachment belt 163. Therefore, by driving the piezoelectric motor 200 mounted in the second unit 120, the second unit 120 rotates with respect to the first unit 110 to thereby make it possible to assist in bending and stretching the first joint. Further, by driving the piezoelectric motor 200 mounted in the third unit 140, the third unit 140 rotates with respect to the second unit 120 to thereby make it possible to assist in bending and stretching the second joint. Further, by driving the piezoelectric motor 200 mounted in the fourth unit 160, the fourth unit 160 rotates with respect to the third unit 140 to thereby make it possible to assist in bending and stretching the third joint.

Since the finger assistive device 100 shown in FIG. 18 bends in a direction intersecting with the bending direction of the index finger 10 at the positions of the elastically deformable section 130*g* of the output member 130 of the second unit 120, the elastically deformable section 150*g* of the output member 150 of the third unit 140, and an elastically deformable section 170*g* of the output member 170 of the fourth unit 160, it becomes possible to assist in bending and stretching the first through third joints without hindering the motion in directions other than the bending direction of the index finger 10. Further, by deforming the output member 130 of the second unit 120 at the position of the elastically deformable section 130*g*, or deforming the output member 150 of the third unit 140 at the position of the elastically deformable section 150*g*, the finger assistive device 100 can be customized (adjusted) so as to fit the shapes of the first joint and the second joint of the index finger 10 similarly to the first embodiment described above.

Although the finger assistive devices 100 according to the embodiments and the modified examples are hereinabove explained, the invention is not limited to each of the embodiments and the modified examples described above, but can be put into practice in various forms within the scope or the spirit of the invention.

The invention can be applied to rehabilitation of a finger operation to a person with paralysis due to a stroke or the like, and further to teaching of finger operations (e.g., transfer of proficient skills and acquisition of new actions) to healthy people.

The entire disclosure of Japanese Patent Application No. 2013-206153, filed Oct. 1, 2013 is expressly incorporated by reference herein.

What is claimed is:

1. A finger assistive device to be mounted to a finger and adapted to assist a bending action of the finger, comprising:
   a first member to be mounted to the finger; and
   a second member to be mounted to the finger, and connected to the first member so as to be rotatable in a bending direction of the finger,
   wherein either one of the first member and the second member includes a relative position changing section adapted to change a relative position of the second member to the first member around a second axis different from the first axis, and
   wherein the relative position changing section makes bending deformation to thereby change a relative position of the second member to the first member.

2. The finger assistive device according to claim 1, wherein
   the relative position changing section is provided with at least one through hole.

3. The finger assistive device according to claim 2, wherein
   a plurality of the through holes are arranged in a predetermined direction.

4. The finger assistive device according to claim 2, wherein
   the through hole is formed to have an elongated shape elongated in a predetermined direction.

5. The finger assistive device according to claim 1, further comprising:
   a third member to be mounted to one of the finger and a base of the finger, and connected to the second member so as to be rotatable in a bending direction of the finger,
   wherein either one of the second member and the third member includes a relative position changing section adapted to change a relative position of the third member to the second member in a direction different from the rotatable direction.

6. The finger assistive device according to claim 5, further comprising:
   a fourth member to be mounted to the base of the finger, and connected to the third member to be mounted to the finger so as to be rotatable in a bending direction of the finger,
   wherein either one of the third member and the fourth member includes a relative position changing section adapted to change a relative position of the fourth member to the third member in a direction different from the rotatable direction.

7. The finger assistive device according to claim 1, wherein
   the relative position changing section is included in the second member, and
   the first member and the relative position changing section are rotatably connected to each other.

8. The finger assistive device according to claim 1, wherein
   the relative position changing section makes torsional deformation to thereby change a relative position of the second member to the first member.

9. The finger assistive device according to claim 1, wherein
   the relative position changing section makes plastic deformation to thereby change the relative position of the second member to the first member.

10. The finger assistive device according to claim 1, wherein
    the relative position changing section is provided with a groove.

11. The finger assistive device according to claim 1, wherein
    the relative position changing section is provided with a cutout.

12. The finger assistive device according to claim 1, wherein
    the relative position changing section is formed of a material low in rigidity compared to a part other than the relative position changing section in one of the first member and the second member.

13. The finger assistive device according to claim 1, wherein
    the relative position changing section expands and contracts a distance between the first member and the second member.

14. The finger assistive device according to claim 1, wherein the finger assistive device is configured to be disposed on a lateral side of a finger such that the relative position changing section accounts for lateral displacement of a first joint of the finger relative to a second joint of the finger away from a vertical axis through the second joint of the finger.

15. A finger assistive device comprising:
    a first member; and
    a second member connected to the first member so as to be rotatable in a predetermined direction around a first axis,
    wherein either one of the first member and the second member includes a relative position changing section adapted to change a relative position of the second member to the first member around a second axis different from the first axis,
    the first member includes a first ring section in which a finger can be inserted, and
    the second member includes a second ring section in which a finger can be inserted.

* * * * *